(12) United States Patent
Berry et al.

(10) Patent No.: US 9,969,668 B2
(45) Date of Patent: May 15, 2018

(54) METHODS AND INDUSTRIAL PROCESSES FOR THE PRODUCTION OF FREE FATTY ACIDS AND DERIVATIVES THEREOF FROM SOAP STOCKS

(71) Applicant: INVENTURE RENEWABLES, INC., Tuscaloosa, AL (US)

(72) Inventors: William W. Berry, Tuscaloosa, AL (US); William Rusty Sutterlin, Tuscaloosa, AL (US); Mark G. Tegen, Tuscaloosa, AL (US); Nathan Killingsworth, Tuscaloosa, AL (US)

(73) Assignee: INVENTURE RENEWABLES, INC., Tuscaloosa, AL (US)

( * ) Notice: Subject to any disclaimer, the term of this patent is extended or adjusted under 35 U.S.C. 154(b) by 0 days. days.

(21) Appl. No.: 14/913,603

(22) PCT Filed: Aug. 29, 2014

(86) PCT No.: PCT/US2014/053584
§ 371 (c)(1),
(2) Date: Feb. 22, 2016

(87) PCT Pub. No.: WO2015/031857
PCT Pub. Date: Mar. 5, 2015

(65) Prior Publication Data
US 2016/0201010 A1    Jul. 14, 2016

Related U.S. Application Data

(60) Provisional application No. 61/990,506, filed on May 8, 2014, provisional application No. 61/872,429, filed on Aug. 30, 2013.

(51) Int. Cl.
*C07C 51/15* (2006.01)
*C11C 1/02* (2006.01)
(Continued)

(52) U.S. Cl.
CPC .............. *C07C 51/15* (2013.01); *C07C 51/02* (2013.01); *C10L 1/026* (2013.01); *C11C 1/002* (2013.01);
(Continued)

(58) Field of Classification Search
CPC ......... C11C 1/002; C11C 3/003; C11C 1/025; C07C 67/00; C07C 51/00; C07C 51/02; C07C 51/15
See application file for complete search history.

(56) References Cited

U.S. PATENT DOCUMENTS 1,946,419 A * 2/1934 Woodruff ................ C07C 51/02
562/405
2,232,331 A * 2/1941 Leithe ..................... C07C 51/02
530/209

(Continued)

OTHER PUBLICATIONS

Young, International Search Report and Written Opinion for PCT/US2014/053584 dated Apr. 6, 2015.

*Primary Examiner* — Yate' K Cutliff
(74) *Attorney, Agent, or Firm* — Greer, Burns & Crain; Gregory P. Einhorn

(57) ABSTRACT

This invention generally relates to the production of free fatty acids and/or derivatives thereof, e.g. fatty acid alkyl esters, from soapstock comprising soaps (salts of fatty acids). In alternative embodiments, the invention provides methods and industrial processes for generating free fatty acids and/or fatty acid derivatives from a soapstock comprising soaps by combining the feedstock with one or more reactants to form a reaction mixture and reacting the mixture at a temperature and pressure sufficient to provide for the acidification of the soaps.

25 Claims, 5 Drawing Sheets

(51) Int. Cl.
*C07C 51/02* (2006.01)
*C11C 1/00* (2006.01)
*C11C 3/00* (2006.01)
*C10L 1/02* (2006.01)

(52) U.S. Cl.
CPC .............. *C11C 1/025* (2013.01); *C11C 3/003* (2013.01); *C10L 2200/0476* (2013.01); *C10L 2270/026* (2013.01); *Y02E 50/13* (2013.01); *Y02E 50/16* (2013.01)

(56) References Cited

U.S. PATENT DOCUMENTS

| | | | | |
|---|---|---|---|---|
| 2,895,976 | A * | 7/1959 | Kairys | C07C 51/487 554/177 |
| 3,901,869 | A * | 8/1975 | Bills | C07C 51/02 530/209 |
| 5,286,845 | A | 2/1994 | Huibers et al. | |
| 2009/0069585 | A1 | 3/2009 | Halpern | |
| 2011/0195471 | A1 | 8/2011 | Berry et al. | |
| 2014/0135515 | A1* | 5/2014 | Dasari | C11B 3/04 554/212 |

* cited by examiner

US 9,969,668 B2

METHODS AND INDUSTRIAL PROCESSES FOR THE PRODUCTION OF FREE FATTY ACIDS AND DERIVATIVES THEREOF FROM SOAP STOCKS

RELATED APPLICATIONS

This application is a national phase application claiming benefit of priority under 35 U.S.C. § 371 to Patent Convention Treaty (PCT) International Application serial no. PCT/US2014/053584, filed Aug. 29, 2014, which claims the benefit of priority under 35 U.S.C. § 119(e) of U.S. Provisional Application Ser. No. 61/872,429, filed Aug. 30, 2013, and U.S. Ser. No. 61/990,506, filed May 8, 2014. The aforementioned applications are expressly incorporated herein by reference in their entirety and for all purposes.

FIELD OF THE INVENTION

This invention generally relates to the treatment of feedstocks comprising soaps, or fatty acid salts, produced during the refining of natural oils. In alternative embodiments, the invention provides methods and industrial processes for generating free fatty acids, fatty acid alkyl esters, or a combination thereof, comprising directly contacting a soap, e.g., a soapstock material, with a system comprising water, $CO_2$ and, optionally, an alcohol whereby the partial pressure of the system provides for acidification, solvolysis (such as alcoholysis or esterification), or a combination thereof, of the soap material at reduced temperatures and pressures.

BACKGROUND

Fatty acids and their derivatives, e.g. fatty acid alkyl esters, are commercially valuable as chemical intermediates as well as fuels. For example, fatty acid methyl esters (FAME), derived from vegetable oils, are used as an alternative to fossil-derived diesel fuels. Currently, the majority of biodiesel is produced via base-catalyzed trans-esterification of triglycerides contained in natural oils. However, the conversion of fats or oils that may otherwise be used for food or animal feeds is not desirable. Soaps (salts of fatty acids) that are produced during the vegetable oil refining process represent an alternative source of free fatty acids and do not compete with food or animal feeds.

Crude vegetable oils typically undergo several refining steps to remove fatty acids and other impurities. During alkali refining, the standard refining method for crude soybean and other vegetable oils, fatty acids present in the crude oils are neutralized using a base, e.g. sodium hydroxide, and separated from solution in an aqueous form. The separated product, commonly referred to as "soapstock" comprises primarily soaps, as well as varying levels of other lipid products including mono-, di- and triglycerides, un-neutralized fatty acids, and phosphatides.

Several methods for processing soapstock into free fatty acids or alkyl esters are known in the art. Some of the prior approaches rely on the use of strong acids, such as sulfuric or hydrochloric acids, to acidify the soaps to generate free fatty acids. Other approaches involve the use of an acidic resin and moving bed chromatography to generate fatty acid alkyl esters from soaps. The techniques in the prior art for generating fatty acids and fatty acid derivatives rely on the use of expensive and/or environmentally degrading chemicals, complex reactions requiring long residence times, or some combination thereof. Because soapstock is only available in relatively small quantities relative to the volumes of oil processed during vegetable oil refining, an economically efficient method for converting soapstock into free fatty acids and derivatives thereof should use inexpensive, widely available chemical reactants and mild process conditions.

SUMMARY OF THE INVENTION

In alternative embodiments, the invention provides method and industrial processes for the production of free fatty acids, fatty acid alkyl esters, or a combination thereof from a soap or a soapstock comprising soaps or salts of fatty acids, the method or industrial process comprising:

(a) providing a reaction mixture comprising a soap or a soapstock, water, carbon dioxide ($CO_2$);
and optionally an alcohol or a phase transfer catalyst, wherein the water and $CO_2$ react to form carbonic acid, wherein optionally the alcohol is selected from the group consisting of a methanol, ethanol, propanol, butanol, isopropyl alcohol, sec-butanol, t-butanol, benzyl alcohol and a combination thereof; and
(b) reacting the reaction mixture at:
a temperature in the range of between about 0° C. and about 50° C., or about 5° C. to about 40° C., about 10° C. to about 30° C., or about 15° C. to about 25° C., and
a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi,
for a time that is sufficient to provide for the acidification of a portion of, or substantially all of, the soaps,
wherein optionally the time is between about 0 to about 24 hours, between about 0 to about 12 hours, e.g. between about 1 hour and about 8 hours, between about 3 hours and 5 hours, between about 5 minutes and one hour, between about 2 minutes to about 20 minutes, or between about 0 minutes to about 1 minute,
thereby generating free fatty acids and a bicarbonate from the soaps, and, optionally, esterifying at least a portion of the free fatty acids.

In alternative embodiments, the soapstock further comprises glycerides and/or phosphatides and the glycerides and/or phosphatides are subjected to hydrolysis and/or esterification, thereby generating free fatty acids and/or fatty acid alkyl esters.

In alternative embodiments, the soapstock is derived from a crude vegetable oil selected from the group consisting of: soybean oil, palm oil, canola oil, rapeseed oil, wheat germ oil, safflower oil, peanut oil, cottonseed oil, sunflower oil, and algae oil.

In alternative embodiments, the amount of water in the reaction mixture is between about 1 mol to about 200 mol per mol, or between about 10 and 100 mol per mol, of soapstock.

In alternative embodiments, the amount of $CO_2$ in the reaction mixture is between about 1 mol to about 70 mol per mol, or between about 10 mol to about 60 mol per mol, or about 10, 20, 30, 40, 50, 60, 70, 80, 90 or 100 or more mol per mol, of soapstock.

In alternative embodiments, the alcohol in the reaction mixture is between about 1 mol to about 200 mol per mol, between about 5 mol to about 150 mol per mol, or between about 10 and 100 mol per mol, or about 10, 20, 30, 40, 50, 60, 70, 80, 90 or 100 or more mol per mol, of soapstock.

In alternative embodiments, the optional phase transfer catalyst in the reaction mixture is between about 1 wt % to about 50 wt % of the reaction mixture, or is between about 1, 5, 10, 20, 30, 40, 50, 60, 70, 80 or 90 wt % of the reaction mixture.

In alternative embodiments, the optional phase transfer catalyst is ammonium chloride. In alternative embodiments, the optional phase transfer catalyst is selected from the group consisting of ammonium chloride, tetrabutyl-ammonium bromide, tetraethyl-ammonium bromide and a combination thereof.

In alternative embodiments, the invention provides methods and industrial processes for the production of free fatty acids and/or fatty acid alkyl esters from a soap or a soapstock comprising soaps or salts of fatty acids, the method or industrial process comprising:

(a) providing a reaction mixture comprising a soap or a soapstock, water, and carbon dioxide ($CO_2$);

wherein optionally the alcohol is selected from the group consisting of a methanol, ethanol, propanol, butanol, isopropyl alcohol, sec-butanol, t-butanol, benzyl alcohol and a combination thereof and (b) reacting the reaction mixture at:

a temperature in the range of about 0° C. and about 50° C., or about 5° C. to about 40° C., about 10° C. to about 30° C., or about 15° C. to about 25° C., and a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi, for a time that is sufficient to provide for the acidification and esterification of a portion of, or substantially all of, the soaps, wherein optionally the time is between about 0 to about 24 hours, between about 0 to about 12 hours, e.g. between about 1 hour and about 8 hours, between about 3 hours and 5 hours, between about 5 minutes and one hour, between about 2 minutes to about 20 minutes, or between about 0 minutes to about 1 minute, thereby generating free fatty acids, fatty acid alkyl esters and a bicarbonate.

In alternative embodiments, the soapstock is derived from a crude vegetable oil selected from the group consisting of a soybean oil, palm oil, canola oil, rapeseed oil, wheat germ oil, safflower oil, peanut oil, cottonseed oil, sunflower oil, and algae oil.

In alternative embodiments, the amount of water in the reaction mixture is between about 1 mol to about 200 mol per mol, or between about 10 and 100 mol per mol, of soapstock, or about 10, 20, 30, 40, 50, 60, 70, 80, 90 or 100 or more mol per mol, of soapstock.

In alternative embodiments, the amount of $CO_2$ in the reaction mixture is between about 1 mol to about 70 mol per mol, or between about 10 mol to about 60 mol per mol, or about 10, 20, 30, 40, 50, 60, 70, 80, 90 or 100 or more mol per mol, of soapstock.

In alternative embodiments, the invention provides methods and industrial processes for the production of free fatty acids from a soap or a soapstock comprising soaps or salts of fatty acids, the method or industrial process comprising:

(a) providing a reaction mixture comprising a soap or a soapstock, water, an alcohol and carbon dioxide ($CO_2$), wherein optionally the alcohol is selected from the group consisting of a methanol, ethanol, propanol, butanol, isopropyl alcohol, sec-butanol, t-butanol, benzyl alcohol and a combination thereof; and (b) reacting the reaction mixture at:

a temperature in the range of between about 0° C. and about 50° C., or about 5° C. to about 40° C., about 10° C. to about 30° C., or about 15° C. to about 25° C., and a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi, for a time that is sufficient to provide for the acidification of a portion of, or of substantially all of, the soaps, and, the esterification of at least a portion of the free fatty acids, wherein optionally the time is between about 0 to about 24 hours, between about 0 to about 12 hours, e.g. between about 1 hour and about 8 hours, between about 3 hours and 5 hours, between about 5 minutes and one hour, between about 2 minutes to about 20 minutes, or between about 0 minutes to about 1 minute, thereby generating free fatty acids and a bicarbonate, and fatty acid alkyl esters.

In alternative embodiments, the soapstock is derived from a crude vegetable oil selected from the group consisting of: soybean oil, palm oil, canola oil, rapeseed oil, wheat germ oil, safflower oil, peanut oil, cottonseed oil, sunflower oil, and algae oil.

In alternative embodiments, the amount of water in the reaction mixture is between about 1 mol to about 200 mol per mol, or between about 10 and 100 mol per mol, or about 10, 20, 30, 40, 50, 60, 70, 80, 90 or 100 or more mol per mol, of soapstock.

In alternative embodiments, the amount of $CO_2$ in the reaction mixture is between about 1 mol to about 70 mol per mol, or between about 10 and 60 mol per mol, or about 10, 20, 30, 40, 50, 60, 70, 80, 90 or 100 or more mol per mol, of soapstock.

In alternative embodiments, the amount of alcohol in the reaction mixture is between about 1 mol to about 200 mol per mol, or between about 10 and 100 mol per mol, or about 10, 20, 30, 40, 50, 60, 70, 80, 90, 100, 150, 175 or more mol per mol, of soapstock.

In alternative embodiments, the invention provides methods and industrial processes for the production of free fatty acids from a soap or a soapstock comprising soaps (salts of fatty acids), the method or industrial process comprising:

(a) providing a reaction mixture that comprises the soap or soapstock, water, a phase transfer catalyst, and carbon dioxide ($CO_2$); and (b) reacting the reaction mixture at:

a temperature in the range of between about 0° C. and about 50° C., or about 5° C. to about 40° C., about 10° C. to about 30° C., or about 15° C. to about 25° C., and a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi, for a time that is sufficient to provide for the acidification of a portion of, or substantially all of, the soaps, wherein optionally the time is between about 0 to about 24 hours, between about 0 to about 12 hours, e.g. between about 1 hour and about 8 hours, between about 3 hours and 5 hours, between about 5 minutes and one hour, between about 2 minutes to about 20 minutes, or between about 0 minutes to about 1 minute, thereby generating free fatty acids and a bicarbonate.

In alternative embodiments, the soapstock is derived from a crude vegetable oil selected from the group consisting of:

a soybean oil, palm oil, canola oil, rapeseed oil, wheat germ oil, safflower oil, peanut oil, cottonseed oil, sunflower oil, and algae oil.

In alternative embodiments, the amount of water in the reaction mixture is between about 1 mol to about 200 mol per mol, or between about 10 and 100 mol per mol, or about 10, 20, 30, 40, 50, 60, 70, 80, 90 or 100 or more mol per mol, of soapstock.

In alternative embodiments, the amount of $CO_2$ in the reaction mixture is between about 1 mol to about 70 mol per mol, or between about 10 and 60 mol per mol, or about 10, 20, 30, 40, 50, 60, 70, 80, 90 or 100 or more mol per mol, of soapstock.

In alternative embodiments, the optional phase transfer catalyst in the reaction mixture is between about 1 wt % to about 50 wt %, or between about 5 wt % and 40% wt %, of the reaction mixture, or is between about 1, 5, 10, 20, 30, 40, 50, 60, 70, 80 or 90 wt % of the reaction mixture.

In alternative embodiments, the optional phase transfer catalyst is an ammonium chloride. In alternative embodiments, the optional phase transfer catalyst is selected from the group consisting of: an ammonium chloride, tetrabutyl-ammonium bromide, tetraethyl-ammonium bromide and a combination thereof.

In alternative embodiments, the invention provides methods and industrial processes for the production of free fatty acids, fatty acid alkyl esters, or a combination thereof, from a soap or a soapstock comprising soaps or salts of fatty acids, the method or industrial process comprising:

a. providing a reaction mixture comprising a soap or a soapstock, water, carbon dioxide ($CO_2$), wherein the water and $CO_2$ react to form carbonic acid; and b. reacting the reaction mixture at:

a temperature of about 15° C., 16° C., 17° C., 18° C., 19° C., 20° C., 21° C., 22° C., 23° C., 24° C., 25° C., 26° C., 27° C., 28° C., 29° C. or 30° C. or more, or in the range of between about 20° C. and 30° C., or in the range of between about 16° C. and 26° C., or between about 20° C. and about 100° C., or at about room temperature, and a pressure in the range of between about 500 psi and about 1000 psi, or about 600 psi, or between about 100 psi and about 1200 psi, or about 50, 100, 200, 300, 400, 500, 600, 700, 800, 900, 1000, 1100 or 1200 or more psi, for a time that is sufficient to provide for the acidification of a portion of, or substantially all of, the soaps, wherein optionally the time is between about 0 to about 100 minutes, or between about 10 and 90 minutes, or between about 20 and 60 minutes, or about 5, 10, 20, 25, 30, 35, 40, 45, 50, 55 or 60 or more minutes, thereby generating a lipid product comprising free fatty acids and, optionally esters, e.g. glycerides, phospholipids, or both, and a bicarbonate from the soaps; and c. providing a second reaction mixture comprising the lipid product, water, and an alcohol; and reacting the second reaction mixture at:

a temperature in the range of between about 150° C. to about 300° C., or between about 100° C. to about 350° C., and a pressure in the range of between about 1500 psi to about 2500 psi, or between about 1000 psi to about 3000 psi, for a time that is sufficient to provide for the esterification of substantially all of the free fatty acids and the transesterification of substantially all of the esters, wherein optionally the time is between about 0 to about 100 minutes, or between about 10 and 90 minutes, or between about 20 and 60 minutes, or about 5, 10, 20, 25, 30, 35, 40, 45, 50, 55 or 60 or more minutes, thereby generating a reaction product comprising fatty acid alkyl esters and glycerol.

In alternative embodiments, the invention provides methods or industrial processes substantially as hereinbefore described, or as substantially described in FIG. 1, FIG. 2, FIG. 3 or FIG. 4. In alternative embodiments, the invention provides methods or industrial processes comprising a process as set forth in FIG. 1, FIG. 2, FIG. 3 or FIG. 4.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DETAILED DESCRIPTION OF THE INVENTION

Figure 1:
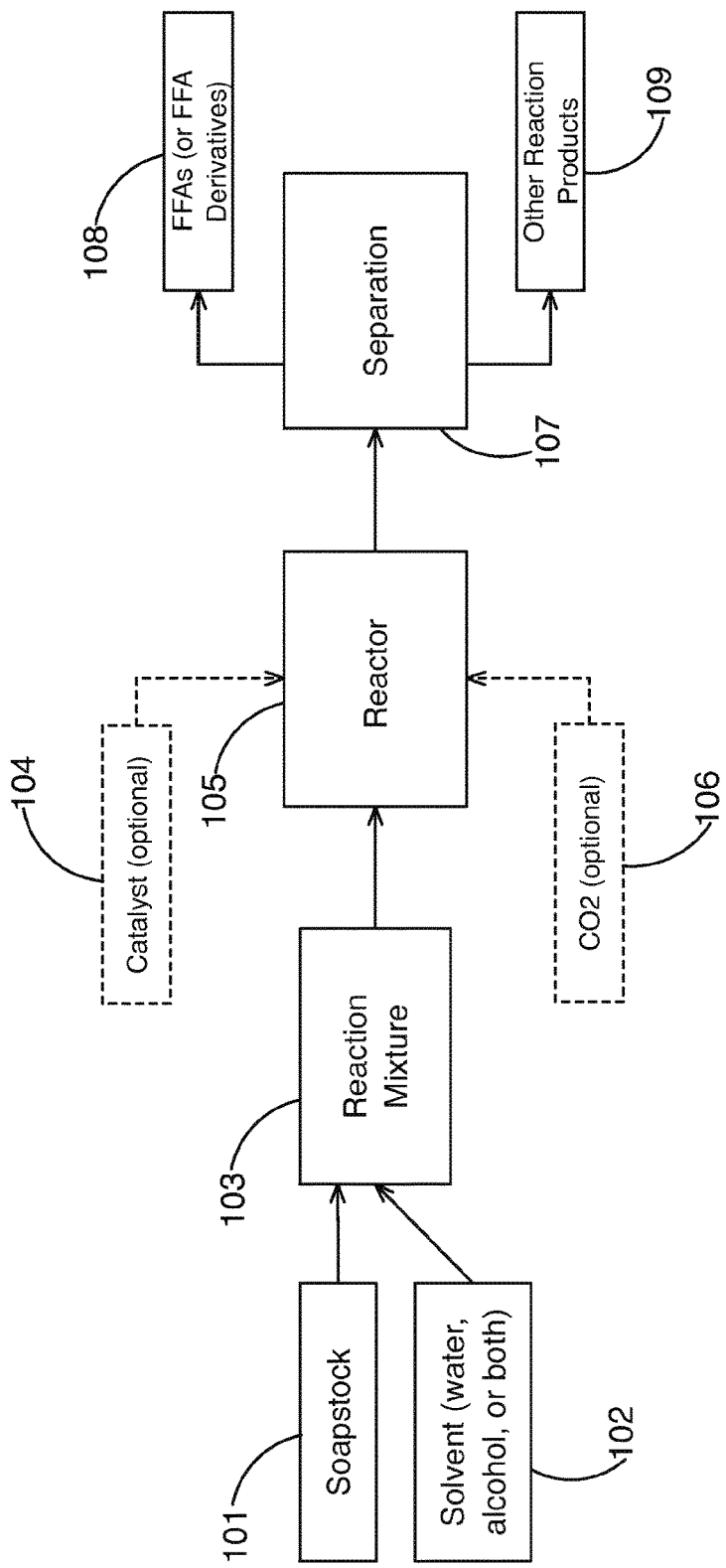
FIG. 1 is a schematic diagram of an exemplary method of the method of the invention comprising producing free fatty acids and other molecules, as described below, from soapstock, as described in detail, below.

In alternative embodiments, the invention provides methods and industrial processes for processing and generating free fatty acids, fatty acid alkyl esters, or a combination thereof, from a soapstock comprising soaps (i.e. salts of fatty acids), as well as other lipid impurities such as glycerides, e.g. mono-, di- or triglycerides, phosphatides, free fatty acids, or a combination thereof. The soapstock can be, for example, a waste stream produced during neutralization stage of the alkali refining of a natural oil such as wheat germ oil, corn oil, soybean oil, safflower oil, peanut oil, cottonseed oil, sunflower oil, rapeseed oil, palm oil, canola oil, algae oil, or other animal or vegetable oils.

In alternative embodiments, the invention provides methods and industrial processes for processing soaps produced during the refining of vegetable oils into free fatty acids and alkyl ester products. In alternative embodiments, the invention provide processes for the generation of free fatty acids, fatty alkyl esters, or a combination thereof, from a soap stock, the exemplary process of the invention comprising providing a feedstock comprising primarily alkali soaps of fatty acids, fatty acids, and glycerides; then, combining this feedstock with water, carbon dioxide and an alcohol (to make a "starting mixture"), and subjecting the starting mixture to a temperature in a range of between about 0° C.

and about 50° C., or between about 10° C. and about 150° C., or about 150° C. and about 300° C., at a pressure of between about 1500 to 2500 psi.

In alternative embodiments, in view of deficiencies in the prior approaches for the generation of free fatty acids and fatty acid alkyl esters from soapstock, the invention provides methods and industrial processes for the efficient, economical conversion of soaps to fatty acids, fatty acid derivatives, or a combination thereof.

In alternative embodiments, the invention provides methods and industrial processes for generating free fatty acids, fatty acid alkyl esters, or a combination thereof, comprising directly contacting a soapstock material with a system comprising water, $CO_2$ and, optionally, an alcohol or a phase transfer catalyst whereby the partial pressure of the system provides for acidification, alcoholysis, esterification or a combination thereof of the material at reduced temperatures and pressures.

The soapstock can be comprised of from about 0 wt % (weight percent) to about 100 wt % soaps, e.g. from about 5 wt % to about 99 wt % soaps, or about 15 wt % soaps to about 85 wt % soaps. The soapstock can contain about 0 wt % to about 100 wt % phospholipids, e.g. from about 5 wt % to about 50 wt % phospholipids. The feedstock can contain from about 1 wt % to about 100 wt % FFA, e.g. from about 5 wt % to about 20 wt % FFA. The feedstock can contain from about 0 wt % to about 100 wt % glycerides e.g. from about 10 wt % to about 50 wt % glycerides. Each of the amounts for the components listed above is based on the dry weight of the feedstock.

In alternative embodiments, the invention provides methods and industrial processes for the production of free fatty acids and/or derivatives thereof from soaps, e.g., soapstocks, comprising providing a reaction mixture that comprises a soap or soapstock, water, $CO_2$, and, optionally, an alcohol or a phase transfer catalyst such as ammonium chloride, and reacting the mixture at a temperature in the range of between about 0° C. and about 50° C., or about 150° C. and about 300° C., or about 5° C. to about 40° C., about 10° C. to about 30° C., or about 15° C. to about 25° C., and a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi, for a time that is sufficient to provide for the acidification of a portion of, or substantially all of, the soaps, thereby generating free fatty acids and a bicarbonate from the soaps, and, optionally, esterifying at least a portion of the free fatty acids.

In alternative embodiments, methods and industrial processes are provided for the production of free fatty acids and from soaps comprising providing a reaction mixture that comprises the soapstock, water, and $CO_2$ and reacting a the mixture at a temperature in the range of between about 0° C. and about 50° C., or about 5° C. to about 40° C., about 10° C. to about 30° C., or about 15° C. to about 25° C., and a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi, for a time that is sufficient to provide for the acidification of a portion of, or substantially all of, the soaps, thereby generating free fatty acids and a bicarbonate.

In alternative embodiments, methods and industrial processes are provided for the production of free fatty acids and/or fatty acid alkyl esters from a soapstock comprising providing a reaction mixture that comprises the soapstock, water, an alcohol and $CO_2$, and reacting a the mixture at a temperature in the range of between about 0° C. and about 50° C., or about 5° C. to about 40° C., about 10° C. to about 30° C., or about 15° C. to about 25° C., and a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi, for a time that is sufficient to provide for the acidification of a portion of, or substantially all of, the soaps, thereby generating free fatty acids and a bicarbonate, and, the esterification of at least a portion of the free fatty acids thereby generating fatty acid alkyl esters.

In alternative embodiments, methods and industrial processes are provided for the production of free fatty acids and comprising providing a reaction mixture that comprises the soapstock, water, a phase transfer catalyst, and $CO_2$, and reacting a the mixture at a temperature in the range of between about 0° C. and about 50° C., or about 5° C. to about 40° C., about 10° C. to about 30° C., or about 15° C. to about 25° C., and a pressure in the range of between about 0 psi and about 3000 psi, or in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi, for a time that is sufficient to provide for the acidification of a portion of, or substantially all of, the soaps, thereby generating free fatty acids and a bicarbonate.

In alternative embodiments, acidification of substantially all of the soaps is acidification of 90%, 91%, 92%, 93%, 94%, 95%, 96%, 97%, 98% or 99% or more of the soaps.

In alternative embodiments, as illustrated in FIG. 1, the soapstock 101 is combined with one or more components (e.g., water, alcohol or both) 102 to form a slurry, or a "reaction mixture" 103.

Throughout this disclosure, the term "slurry", "slurry mixture", "reaction slurry" and "reaction mixture" and the like are used to describe a mixture of both pre-reaction and post-reaction products. These terms are not limited to mixtures comprised of a liquid and a solid and be used to describe any mixtures comprised of one or more components in any physical state, e.g. a liquid and a solid, a liquid and a gas, a liquid, a gas, and a solid, a solid and a gas, two or more liquids, two or more solids, two or more gases, etc.

The soapstock, or the soapstock-comprising slurry ("reaction mixture") 103, is then fed to a reactor 105, container or other appropriate vessel, wherein the heat and pressure, or heat or pressure, are sufficient to generate a reaction, or group of reactions simultaneously.

The resulting reaction products are then separated 107 into one or more discrete products which are suitable for sale directly or for upgrading and/or further processing into other products. The possible reactions include, without limitation: 1) acidification of the soaps, thereby generating free fatty acids and a carbonate product, 2) hydrolysis and/or esterification of the glycerides, and/or phosphatides, thereby generating free fatty acids and/or fatty acid alkyl esters 108, and glycerol and or/phosphate or other products 109 3) esterification of the free fatty acids, thereby generating fatty acid alkyl esters.

In alternative embodiments, the reaction comprises the addition of a catalyst 104 such as ammonium chloride In order to achieve acidification of the soaps, $CO_2$ 106 can be supplied to the reactor, vessel or container, resulting in the formation of carbonic acid as the $CO_2$ comes in contact with the water. The formation of carbonic acid serves to acidify the soaps present in the reaction mixture, resulting in the formation of free fatty acids and a carbonate.

The resulting product mixture can comprise a variety of components, depending on the composition of the feedstock and the specific reaction conditions including heat, pressure, residence time, and the relative quantities of the reactants. These products can include, for example, free fatty acids, fatty acid alkyl esters, glycerol, glycerol derivatives or any combination thereof. The products can be further separated into discreet fractions and marketed directly as end products or as chemical intermediates, adding significant value to the soapstock waste stream.

In any of the embodiments, the reactor system can be batch or continuous. There are several conventional pressure vessel systems available that will operate in batch and continuous modes and the process lends itself for "conventional" methods for this stage. In addition, a continuous pipe-type reactor can be used to carry out the reactions. The reactor is a pipe with sufficient residence time to allow for the reaction to complete and is operated under target pressure and temperature range. The pipe allows for reasonable reaction to occur with minimized vessel complexity.

In alternative embodiments, the soapstock is reacted with water, an alcohol and $CO_2$. In such embodiments, the soaps are subjected to acidification, esterification, or a combination thereof, thereby acidifying the soaps to generate fatty acids and, in the same reaction step, esterifying some or all of the generated free fatty acids to generate fatty acid alkyl esters. The presence of the alcohol may also allow for reduced operating temperatures and pressures to achieve the conversion of soaps to free fatty acids and/or fatty acid alkyl esters. In still further embodiments, the reaction mixture includes a phase-transfer catalyst, e.g. an ammonium salt, to increase the solubility of the soaps in the reaction mixture.

The alcohol used in the various embodiments can be, for example, methanol, ethanol, propanol, butanol, isopropyl alcohol, sec-butanol, t-butanol, benzyl alcohol, or a combination thereof. Alcohols containing 1 to 5 carbons can be well suited for use in alternative embodiments of this invention. However, there may be specific situations and conditions wherein higher alcohols could be used. For purposes of this discussion, methanol is used as the alcohol; however, those skilled in the art would understand that other alcohols may be used.

Figure 2:
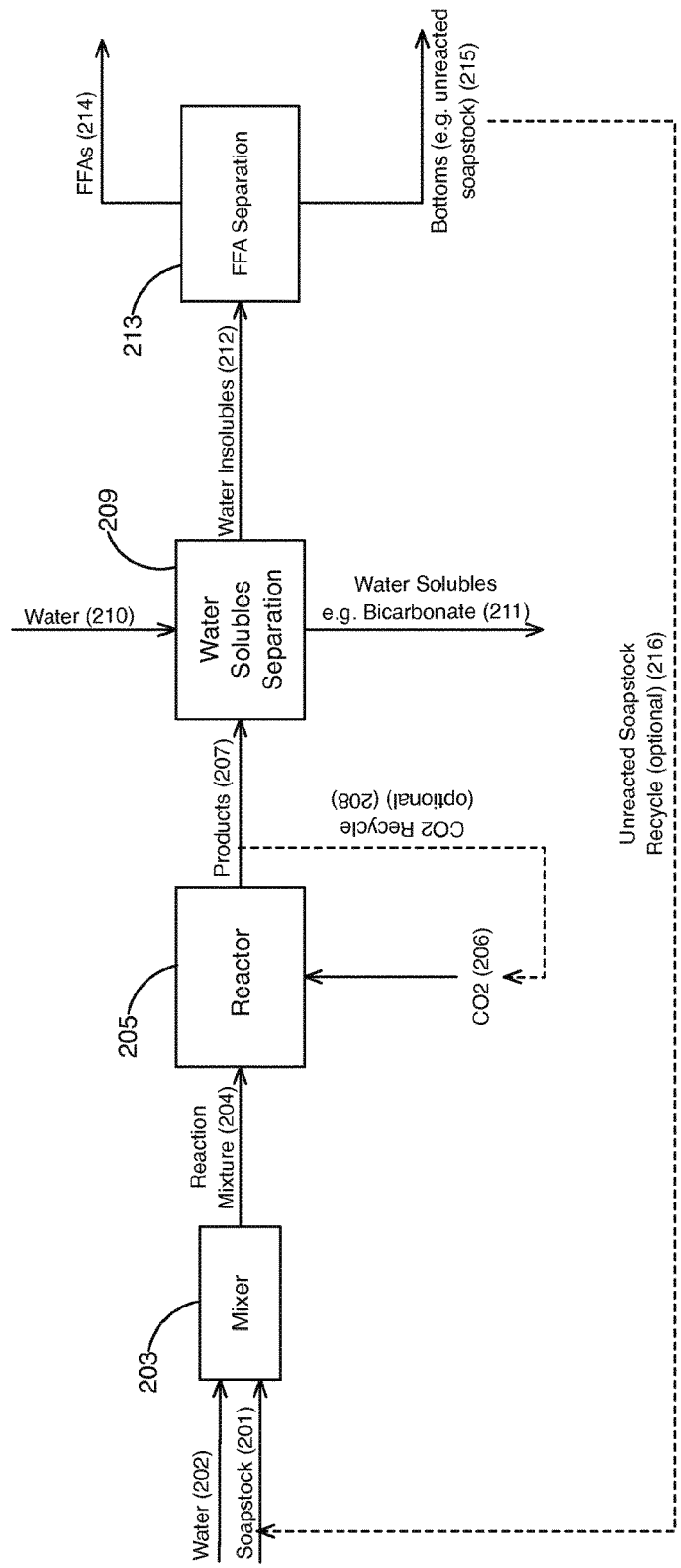
FIG. 2 is a schematic diagram of an exemplary method of the invention comprising producing free fatty acids from soapstock and other molecules, as described below, from soapstock, as described in detail, below.

Single-Stage Process Using Water and $CO_2$:

Referring to FIG. 2, in alternative embodiments, methods of the present invention comprise a single stage process (i.e. a single reaction step). In alternative embodiments, a soapstock 201 is mixed with water 202 in a mixer to form a reaction mixture 203. In alternative embodiments, $CO_2$, is added to the reaction mixture in the mixer 203. In alternative embodiments, $CO_2$ 206, e.g. pressurized gaseous $CO_2$, is fed into the reactor 205 as the soapstock and water mixture enter the reactor 205. In alternative embodiments, the soapstock comprises in addition to soaps: glycerides, e.g. mono- di- and/or triglycerides, other lipids or lipid derivatives, or any combination thereof, as well as other lipid impurities such as glycerides, e.g. mono-, di- or triglycerides, phosphatides, or a combination thereof. The amount of water and $CO_2$ can vary, but would typically be sufficient to allow for a slurry mixture. In alternative embodiments, the $CO_2$ is in a gaseous state when added to the reaction mixture.

In the alternative, the reaction mixture is fed into a reactor 205 or any appropriate container or vessel, wherein the water and the $CO_2$ react to form carbonic acid. The reaction can be carried out at a temperature in the range of between about 0° C. to about 50° C., for example, about 5° C. to about 40° C., about 10° C. to about 30° C., or about 15° C. to about 25° C. The pressure of the reactor, vessel or container can be in the range of between about 0 psi to about 3000 psi, for example in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi.

In the above reaction conditions, the carbonic acid serves to acidify all or a portion of the soaps, thereby generating reaction products 207 comprising free fatty acids and a carbonate. If, for example, the soaps were generated from the crude oil source using sodium hydroxide for the neutralization step, the resulting soaps would be salts of sodium and fatty acids. The above acidification reaction would therefore result in the formation of fatty acids and sodium bicarbonate.

The reaction can be carried out for a period in the range of between about 1 minute and about 300 minutes, e.g. between about 1 minute and 120 minutes, between about 1 minute and about 100 minutes, about 1 minute to about 80 minutes, about 1 minute to about 60 minutes, about 1 minute to about 40 minutes, about 1 minute to about 20 minutes, about 1 minute to about 10 minutes, or about 1 minute to about 5 minutes. The reaction can be carried out for a period in the range of between about 1 hour and 10 hours, or between about 2 hours and 8 hours.

In certain embodiments, an optional recovery step is employed wherein any unreacted $CO_2$ from the reaction is separated from the product stream leaving the reactor and recycled 208 for subsequent reaction 205. Several $CO_2$ recovery methods are known in the art and therefore this step lends itself to conventional methods. In alternative embodiments, un-reacted $CO_2$ can be separated from the product stream, for example, using a flash separation technique wherein the product stream is transferred to a flash drum or appropriate or equivalent vessel wherein the pressure is reduced from the pressure within the reactor, wherein the pressure in the reactor is above the vapor pressure of the $CO_2$ for the corresponding reaction temperature, to a pressure of about atmospheric pressure. The decrease in pressure results in an environment in which the vapor pressure of the $CO_2$ exceeds its external pressure (the pressure of the flash drum of vessel), allowing for the $CO_2$ to vaporize or "flash" out of the product stream.

After the reaction, the resulting products 207 can optionally transferred to a water soluble separation unit 209 wherein the reaction products 207 are mixed, or contacted with water 210 wherein any water soluble products 211, e.g. glycerol, and/or sodium bicarbonate, generated during the reaction are separated from the reaction products that are water insoluble 212. This step can be carried out by any of several suitable methods known in the art, e.g. a water wash and therefore lends itself to conventional methods.

In alternative embodiments, the reaction products are transferred to a static mixer wherein it is mixed with water. The water and reaction product mixture is then transferred to a decanter wherein an oil (lipid) stream comprising the free fatty acids and any unreacted feedstock, and an aqueous stream, comprising bicarbonate, glycerol and/or glycerol derivatives, and any other water soluble reaction products, are formed and are separated.

The aqueous stream (comprising bicarbonate, glycerol and any derivatives thereof) is then transferred to a separating unit wherein glycerol is isolated and removed from the remaining products in the aqueous phase.

In alternative embodiments, the water-insoluble components of the product mixture 212 are then transferred to a free fatty acid (FFA) separation unit 213 wherein the free fatty acids (FFAs) 214 are separated from the other water-insoluble products (the so-called "bottoms") 215, such as unreacted soapstock using conventional methods known in the art, e.g. distillation. The free fatty acids are then available for sale directly as end products or as intermediates for subsequent reaction, e.g. esterification for the production of fatty acid alkyl esters.

Optionally, any unreacted soapstock isolated in the free fatty acid separation unit 213 can be recycled 216 and mixed with for subsequent reactions. In alternative embodiments, unreacted feedstock is recycled and the process is repeated until substantially all of the soaps in the soapstock have been converted to free fatty acids and bicarbonate.

Figure 3:
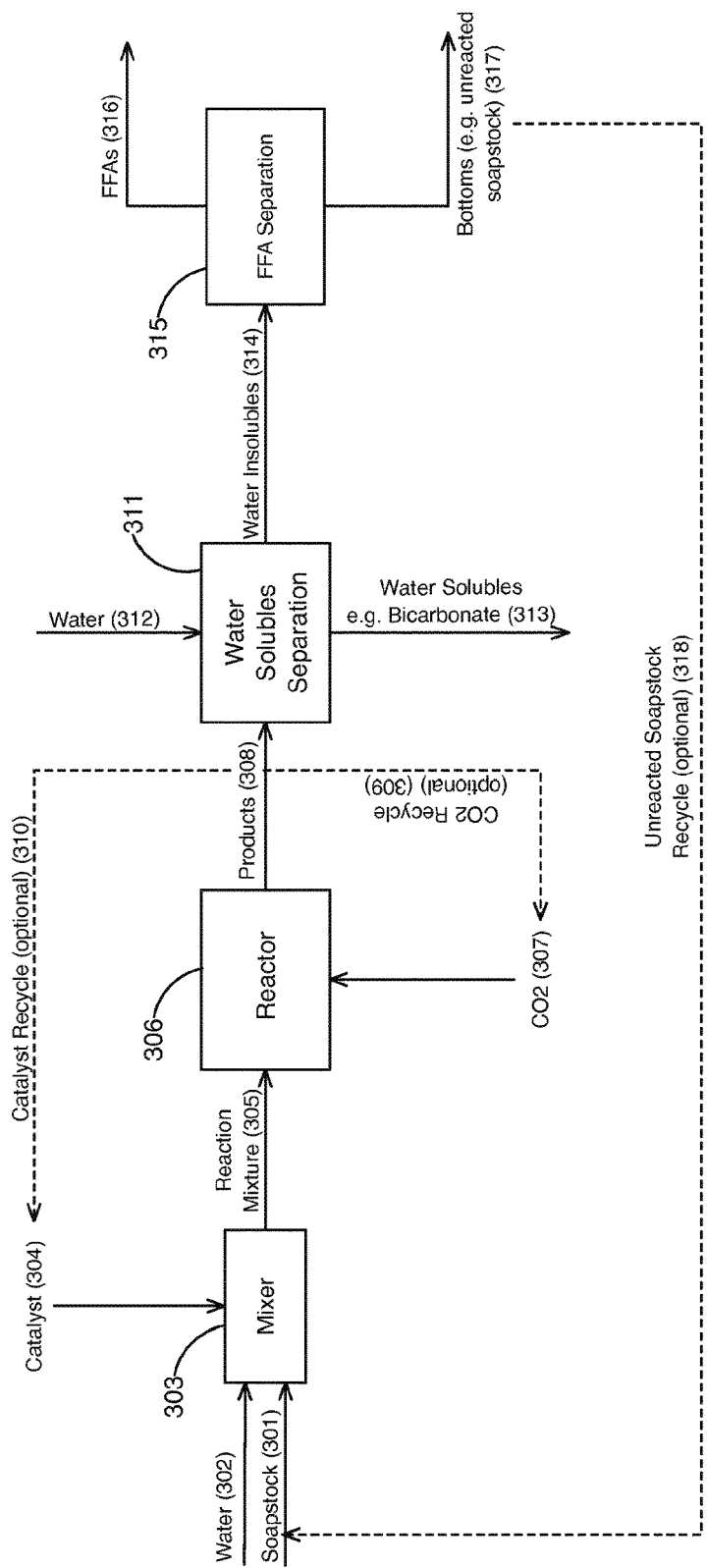
FIG. 3 is a schematic diagram of an exemplary method of the invention comprising producing free fatty acids, alkyl esters, and other molecules, as described below, from soapstock, as described in detail, below.

Single Stage Process with Water, $CO_2$, and Phase Transfer Catalyst:

Referring to FIG. 3, in alternative embodiments, the present invention provides a single stage process (i.e. a single reaction step) for the production of free fatty acids soapstocks comprising reacting the soapstock with water, CO2, and a phase transfer catalyst (PTC). In alternative embodiments an alcohol is added as a solvent in the reaction mixture. In alternative embodiments, a soapstock comprises, in addition to soaps, glycerides, e.g. mono- di- and/or triglycerides, other lipids or lipid derivatives, or any combination thereof. In alternative embodiments, the soapstock 301 is mixed with water 302, $CO_2$, and a PTC 304 to form a reaction mixture. In alternative embodiments, $CO_2$ is fed 307 into the reactor 306 as the soapstock, water, and phase transfer catalyst mixture 305 enters the reactor 306. The amount of water, alcohol, and $CO_2$ can vary, but in alternative embodiments is sufficient to allow for a slurry mixture, e.g. 1 mol of soapstock, 1 mol of water, 1 mol of $CO_2$ and 2 wt % PTC. In alternative embodiments, the $CO_2$ is in a gaseous state when it is added to the reaction mixture.

In alternative embodiments, the reaction mixture 305 is fed into the reactor 306 wherein the water and the $CO_2$ react to form carbonic acid. The reaction can be carried out at a temperature in the range of between about 0° C. to about 50° C., for example, about 5° C. to about 40° C., about 10° C. to about 30° C., or about 15° C. to about 25° C. The pressure of the reactor can be in the range of between about 0 psi to about 3000 psi, for example in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi.

In alternative embodiments, the presence of the phase transfer catalyst (PTC) allows for lower reaction temperatures, pressures, or temperatures and pressures to achieve the desired amount of free fatty production from the soapstock. For example, the temperature of a reaction wherein the reaction mixture comprises a soapstock, water, $CO_2$ and a PTC be room temperature (about 21° C.) and the pressure can be in the range of between about 200 psi to about 300 psi.

In the above reaction conditions, the carbonic acid serves to acidify all or a portion of the soaps, thereby generating free fatty acids and a carbonate. If, for example, the soaps were generated from the crude oil using sodium hydroxide for the neutralization step, the resulting soaps would be salts of sodium and fatty acids. The above acidification reaction would therefore result in the formation of fatty acids and sodium bicarbonate.

The reaction can be carried out for a period in the range of between about 1 minute and about 300 minutes, e.g. between about 1 minute and 120 minutes, between about 1 minute and about 100 minutes, about 1 minute to about 80 minutes, about 1 minute to about 60 minutes, about 1 minute to about 40 minutes, about 1 minute to about 20 minutes, about 1 minute to about 10 minutes, or about 1 minute to about 5 minutes.

In alternative, un-reacted $CO_2$ can be separated from the product stream 308 and recycled 309, for example, using a flash separation technique wherein the product stream is transferred to a flash drum or appropriate or equivalent vessel wherein the pressure is reduced from the pressure within the reactor, wherein the pressure in the reactor is above the vapor pressure of the $CO_2$ for the corresponding reaction temperature, to a pressure of about atmospheric pressure. The decrease in pressure results in an environment in which the vapor pressure of the $CO_2$ exceeds its external pressure (the pressure of the flash drum of vessel), allowing for the $CO_2$ to vaporize or "flash" out of the product stream.

In alternative embodiments, the phase transfer catalyst (PTC) can be isolated and recycled 310 from the product mixture 308 using any method known in the art.

In alternative embodiments, the first reaction mixture 305 also comprises an alcohol, alternatively in the range of 1 to 5 carbons, for example methanol. When present, the alcohol in the first reaction mixture provides increased solvolysis activity such that the fatty acids are more readily generated from the soaps. The addition of the alcohol can also provide for the transesterification of some portion esters in the soapstock to fatty acid alkyl esters. For example, if present, glycerides in the soapstock can react with the alcohol to generate glycerol and fatty acid alkyl esters (if the alcohol is a methanol, the alcohol may also serve to esterify some or all of the fatty acids generated by cleaving the soaps, resulting in the formation of fatty acid alkyl esters. In alternative embodiments, the addition of the alcohol results in less than 10% conversion of the esters and fatty acids present in the soapstock (as well as the fatty acids generated during the reaction resulting from the acidification of the soaps) to fatty acid alkyl esters, e.g. less than about 5% or less than about 4%, 3%, 2%, or less than about 1%.

The alcohol used in this process can be, for example, methanol, ethanol, propanol, butanol, isopropyl alcohol, sec-butanol, t-butanol, benzyl alcohol, or a combination thereof. In some embodiments, alcohols containing 1 to 5 carbons may be preferred, however, there may be specific situations and conditions wherein higher alcohols are used.

In alternative embodiments, the phase transfer catalyst (PTC) 304 can be, for example, ammonium chloride, tetrabutyl-ammonium bromide, tetraethyl-ammonium bromide, or the like.

The reactor system can be batch or continuous. There are several conventional pressure vessel systems available that will operate in batch and continuous modes and the process lends itself to the "conventional" methods for this stage. In addition, a continuous pipe-type or plug-flow reactor can be used to carry out the reaction. The reactor is a pipe with sufficient residence time to allow for the reaction to complete and is operated under the target pressure and temperature range. The pipe allows for reasonable reaction to occur with minimized vessel complexity.

After the reaction, the resulting products 308 can optionally transferred to a water soluble separation unit 311 wherein the reaction products 308 are mixed, or contacted with water 312 and wherein any water soluble products 313, e.g. glycerol, and/or bicarbonate, generated during the reaction are separated from the reaction products that are water insoluble 314. This step can be carried out by any of several suitable methods known in the art, e.g. a water wash, and therefore lends itself to conventional methods.

In alternative embodiments, the reaction products 308 are transferred to a static mixer 311 wherein it is mixed with water 312. The water and reaction product mixture is then transferred to a decanter wherein an oil (lipid) stream comprising the free fatty acids and any unreacted feedstock, and an aqueous stream, comprising bicarbonate, glycerol and/or glycerol derivatives, and any other water soluble reaction products, are formed and are separated.

The aqueous stream 313 (comprising bicarbonate, glycerol and any derivatives thereof) is then transferred to a separating unit wherein glycerol is isolated and removed from the remaining products in the aqueous phase.

In alternative embodiments, the water-insoluble components of the product mixture 314 are then transferred to a free fatty acid (FFA) separation unit 315 wherein the free fatty acids (FFAs) 316 are separated from the other water-insoluble products (the so-called "bottoms") 317, such as unreacted soapstock, using conventional methods known in the art, e.g. distillation. The free fatty acids are then available for sale directly as end products or as intermediates for subsequent reaction, e.g. esterification for the production of fatty acid alkyl esters.

Optionally, any unreacted soapstock isolated in the free fatty acid (FFA) separation unit 315 can be recycled 318 and mixed with for subsequent reactions. In alternative embodiments, unreacted feedstock is recycled and the process is repeated until substantially all of the soaps in the soapstock have been converted to free fatty acids and bicarbonate.

Figure 4:
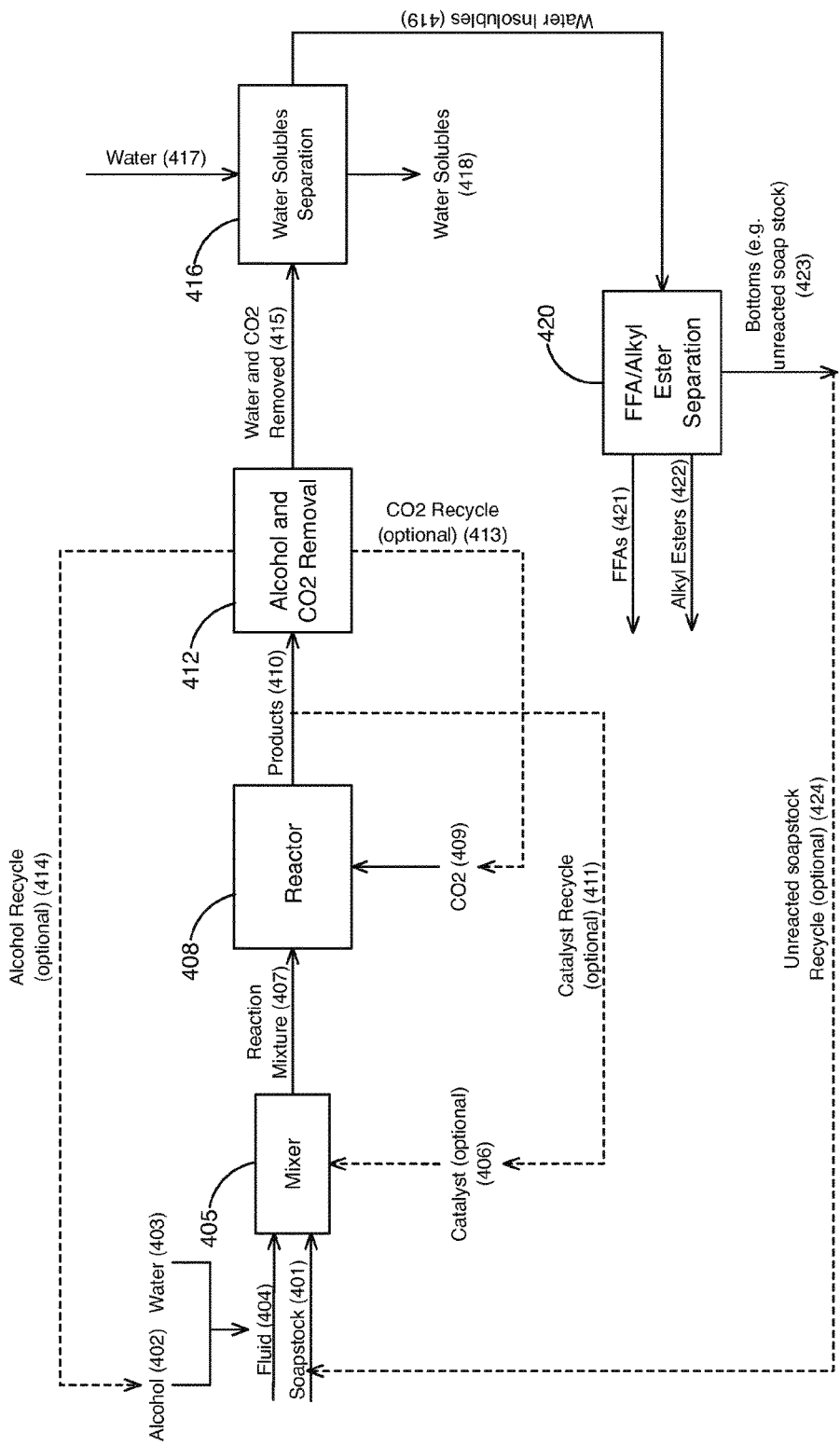
FIG. 4 is a schematic diagram of an exemplary method of the invention comprising producing free fatty acids, alkyl esters, and other molecules, as described below, from soapstock, as described in detail, below.

Single-Stage Process with Water, $CO_2$, and an Alcohol:

Referring to FIG. 4, in alternative embodiments, the present invention provides a single stage process (i.e., single reaction) for the production of free fatty acids and/or fatty acid alkyl esters from soapstocks. In alternative embodiments, a soapstock comprises, in addition to soaps, glycerides, e.g. mono- di- and/or triglycerides, other lipids or lipid derivatives, or any combination thereof, as well as other lipid impurities such as glycerides, e.g. mono-, di- or triglycerides, phosphatides, or a combination thereof.

In alternative embodiments, the soapstock is mixed with water, $CO_2$, and an alcohol to form a reaction mixture. In alternative embodiments, the soapstock 401 is combined with an alcohol 402 and water 403 in a mixer 405 to form a reaction mixture 407, or the soapstock 401 is combined with a fluid 404, comprising the alcohol 402 and the water 403, in a mixer 405 to form a reaction mixture 407.

In alternative embodiments, the $CO_2$ 409 is fed into the reactor 408 as the soapstock, water, and alcohol mixture 407 enters the reactor. The amount of water, alcohol, and $CO_2$ can vary, but would typically be sufficient to allow for a slurry mixture, e.g. 1 mol of soapstock, 1 mol of water, 1 mol of $CO_2$ and 1 mol of alcohol. In alternative embodiments, the $CO_2$ is in a gaseous state when it is added to the reaction mixture or the reactor.

Optionally, the reaction further includes the addition of a Phase Transfer Catalyst (PTC) 406 (e.g., into a mixing compartment 405). In alternative embodiments, the optional PTC can be, for example, ammonium chloride, tetrabutyl-ammonium bromide, tetraethyl-ammonium bromide, or the like. In those embodiments comprising the use of a PTC, the presence of the PTC allows for lower reaction temperatures, pressures, or temperatures and pressures to achieve the desired amount of free fatty production from the soapstock.

In the various embodiments involving the single-stage process, the reaction mixture is fed into the reactor 408 wherein the water and the $CO_2$ react to form carbonic acid. The reaction can be carried out at a temperature in the range of between about 0° C. to about 50° C., for example, about 5° C. to about 40° C., about 10° C. to about 30° C., or about 15° C. to about 25° C. The pressure of the reactor can be in the range of between about 0 psi to about 3000 psi, for example in the range of between about 50 psi and about 2500 psi, about 100 psi to about 2000 psi, about 150 psi to about 1500 psi, about 200 psi to about 1000 psi, about 250 psi to about 800 psi, or about 300 psi to about 600 psi.

In alternative embodiments, the presence of the alcohol allows for lower reaction temperatures, pressures, or temperatures and pressures to achieve the desired amount of free fatty acid and/or fatty acid alkyl ester production from the soapstock. For example, the temperature of a reaction wherein the reaction mixture comprises a soapstock, water, $CO_2$ and an alcohol can be approximately room temperature (about 21° C.) and the pressure can be in the range of between about 200 psi to about 300 psi.

In the above reaction conditions, the carbonic acid serves to acidify all or a portion of the soaps, thereby generating free fatty acids and a carbonate. If, for example, the soaps were generated from the crude oil using sodium hydroxide for the neutralization step, the resulting soaps would be salts of sodium and fatty acids. The above acidification reaction would therefore result in the formation of fatty acids and sodium bicarbonate.

The reaction can be carried out for a period in the range of between about 1 minute and about 300 minutes, e.g. between about 1 minute and 120 minutes, between about 1 minute and about 100 minutes, about 1 minute to about 80 minutes, about 1 minute to about 60 minutes, about 1 minute to about 40 minutes, about 1 minute to about 20 minutes, about 1 minute to about 10 minutes, or about 1 minute to about 5 minutes.

In the above reaction conditions, several reactions can occur simultaneously. The reactions can include, without limitation: acidification of the soaps to generate free fatty acids and a bicarbonate, and esterification of the free fatty acids to generate fatty acid alkyl esters.

The alcohol used in this process can be, for example, methanol, ethanol, propanol, butanol, isopropyl alcohol, sec-butanol, t-butanol, benzyl alcohol, or a combination thereof. In some embodiments, alcohols containing 1 to 5 carbons may be preferred, however, there may be specific situations and conditions wherein higher alcohols are used.

The reactor system can be batch or continuous. There are several conventional pressure vessel systems available that will operate in batch and continuous modes and the process lends itself to the "conventional" methods for this stage. In addition, a continuous pipe-type or plug-flow reactor can be used to carry out the reaction. The reactor is a pipe with sufficient residence time to allow for the reaction to complete and is operated under the target pressure and temperature range. The pipe allows for reasonable reaction to occur with minimized vessel complexity.

In alternative embodiments, the PTC can be isolated and recycled 411 from the product mixture 410 through any of several methods known in the art.

In alternative embodiments, the product mixture 410 can be transferred to an alcohol and $CO_2$ separation unit wherein un-reacted $CO_2$ can be separated from the product mixture 410 and recycled 413, and un-reacted alcohol can be separated from the product mixture 410 and recycled 414. The alcohol and $CO_2$ separation process can comprise, for example, using a flash separation technique wherein the product stream is transferred to a flash drum or appropriate or equivalent vessel wherein the pressure is reduced from the pressure within the reactor, wherein the pressure in the reactor is above the vapor pressure of the $CO_2$ and the alcohol for the corresponding reaction temperature, to a pressure of about atmospheric pressure. The decrease in pressure results in an environment in which the vapor pressure of the $CO_2$ and the alcohol exceeds its external pressure (the pressure of the flash drum of vessel), allowing for the $CO_2$ to vaporize or "flash" out of the product stream.

After the reaction, the resulting products 415 can optionally transferred to a water soluble separation unit 416 wherein the reaction products (wherein the unreacted alcohol and $CO_2$ have been removed) 415 are mixed, or contacted with water 417 and wherein any water soluble products 418, e.g. glycerol, and/or bicarbonate, generated during the reaction are separated from the reaction products that are water insoluble 418. This step can be carried out by any of several suitable methods known in the art, e.g. a water wash and therefore lends itself to conventional methods.

In alternative embodiments, the reaction products are transferred to a static mixer wherein it is mixed with water. The water and reaction product mixture is then transferred to a decanter wherein an oil (lipid) stream comprising the free fatty acids and any unreacted feedstock, and an aqueous stream, comprising bicarbonate, glycerol and/or glycerol derivatives, and any other water soluble reaction products, are formed and are separated.

The aqueous stream (comprising bicarbonate, glycerol and any derivatives thereof) is then transferred to a separating unit wherein glycerol is isolated and removed from the remaining products in the aqueous phase.

In alternative embodiments, the water-insoluble components of the product mixture 419 are then transferred to a free fatty acid/fatty alkyl ester separation unit 420 wherein the free fatty acids 421 fatty acid alkyl esters 422 are separated from the other water-insoluble products (the so-called "bottoms") 423, such as unreacted soapstock using conventional methods known in the art, e.g. distillation. The free fatty acids and fatty acid alkyl esters are then available for sale directly as end products or as intermediates for subsequent reaction, e.g. esterification for the production of fatty acid alkyl esters.

Optionally, any unreacted soapstock isolated in the free fatty acid separation unit 420 can be recycled 424 and mixed with for subsequent reactions. In alternative embodiments, unreacted feedstock is recycled and the process is repeated until substantially all of the soaps in the soapstock have been converted to free fatty acids and bicarbonate.

Figure 5:
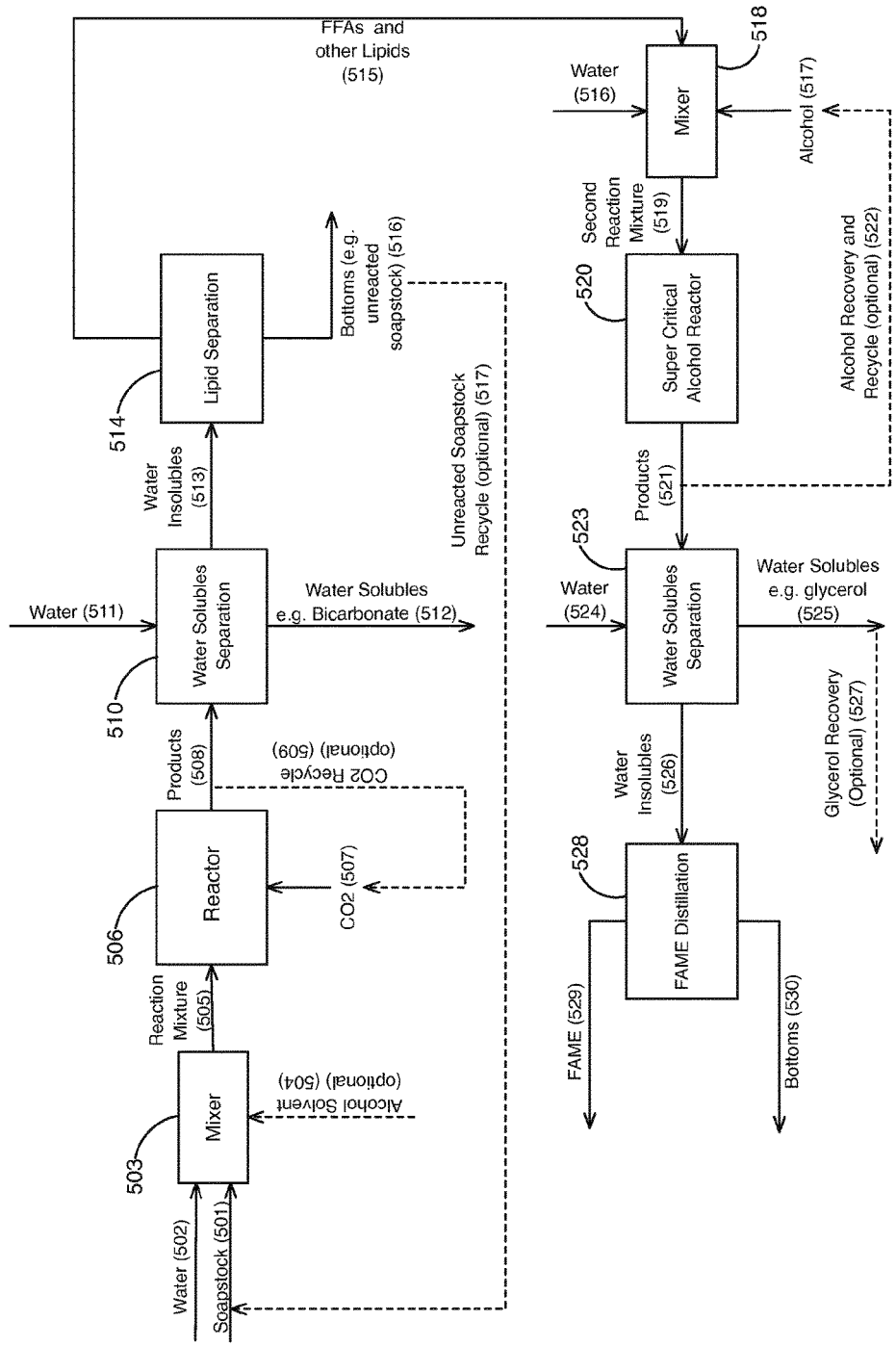
FIG. 5 is a schematic diagram of an exemplary method of the invention comprising producing free fatty acids, alkyl esters, and other molecules, as described below, from soapstock, as described in detail, below.

Two-Stage Process:

Referring to FIG. 5, in alternative embodiments, methods of the present invention comprise a two-stage (i.e. two reactions) process. In the first stage, the soapstock is mixed with water and $CO_2$ prior to entering the reactor. In alternative embodiments, soapstock 501 is mixed with water 502 in a mixer 503 to form a reaction mixture 505. The amount or water and $CO_2$ can vary, but would typically be sufficient to allow for a slurry mixture, e.g. about 1 mol of soapstock and 1 mol of water. After entering the reactor 506, the water and $CO_2$ react to form carbonic acid as follows:

$$CO_2 + H_2O \rightarrow H_2CO_3$$

In alternative embodiments the formation of carbonic acid is desirable in that it will react with soaps to generate free fatty acids and a carbonate. For example, if the soapstock used in the reaction is generated by reacting an un-neutralized vegetable oil with sodium hydroxide, the resulting soapstock would comprise soaps of fatty acids and sodium. The reaction would therefore yield free fatty acids and sodium bicarbonate, which is recovered following the first reaction stage. Any glycerides or other non-soap lipid or ester products in the soapstock proceed through first stage unreacted. In alternative embodiments, some portion of the lipids and/or esters in the soapstock are acidified and/or hydrolyzed in the first stage to generate free fatty acids and glycerol or glycerol derivatives.

The first stage of the two-stage process generates a reaction slurry comprising free fatty acids and un-reacted glycerides. A generalized representation of the reaction in the in the first stage is as follows:

$$\text{Soaps} + \text{glycerides} + H_2CO_3 \rightarrow \text{Free fatty acids} + NaHCO_3 + \text{glycerides}$$

In alternative embodiments, the first stage of the two-stage process is carried out at a temperature in the range of between about 20° C., to about 100° C. for example room temperature, and a pressure of between about 500 psi to about 1000 psi, for example 600 psi. In alternative embodiments, the partial pressure of the CO2 in the reaction mixture is maintained such that the pKa of the carbonic acid in the reactor is less than about 4.4.

In alternative embodiments, the first stage of the reaction is carried at a pH in the range of between about 0 and about 7. In alternative embodiments, the pH of the first stage of the reaction, or any stage of a reaction, or any step of the complete reaction process (e.g., reacting the first starting mixture, versus reacting second or a third mixture), can be anywhere between about pH 0 and pH 7.4, or between about pH 0.5 and pH 7.0, or between about 0 and pH 7, or about pH 1, 1.5, 2, 2.5, 3, 3.5, 4, 4.5, 5, 5.5, 6, 6.5, 7, 7.5 or more (or more basic).

The reaction time of the first stage can be in the range of between about 0 minutes to about 100 minutes, for example about 30 minutes. In alternative embodiments, the reaction time of the first stage, or any stage, is in the range of between about 0 to about 24 hours, between about 0 to about 12 hours, e.g. between about 1 hour and about 8 hours, between about 3 hours and 5 hours, between about 5 minutes and one hour, between about 2 minutes to about 20 minutes, or between about 0 minutes to about 1 minute.

In alternative embodiments, the first reaction mixture also comprises an alcohol 504, alternatively in the range of 1 to 5 carbons, for example methanol. When present, the alcohol in the first reaction mixture provides increased solvolysis activity such that the fatty acids are more readily generated from the soaps. The addition of the alcohol can also provide for the transesterification of some portion esters in the soapstock to fatty acid alkyl esters. For example, if present, glycerides in the soapstock can react with the alcohol to generate glycerol and fatty acid alkyl esters (if the alcohol is a methanol, the alcohol may also serve to esterify some or all of the fatty acids generated by cleaving the soaps, resulting in the formation of fatty acid alkyl esters. In alternative embodiments, the addition of the alcohol as a solvent in the first stage of the reaction results in less than 10% conversion of the esters and fatty acids present in the soapstock (as well as the fatty acids generated during the reaction resulting from the acidification of the soaps) to fatty acid alkyl esters, e.g. less than about 5% or less than about 4%, 3%, 2%, or less than about 1%.

In alternative, un-reacted $CO_2$ can be separated from the product stream 508 and recycled 509, for example, using a flash separation technique wherein the product stream is transferred to a flash drum or appropriate or equivalent vessel wherein the pressure is reduced from the pressure within the reactor, wherein the pressure in the reactor is above the vapor pressure of the $CO_2$ for the corresponding reaction temperature, to a pressure of about atmospheric pressure. The decrease in pressure results in an environment in which the vapor pressure of the $CO_2$ exceeds its external pressure (the pressure of the flash drum of vessel), allowing for the $CO_2$ to vaporize or "flash" out of the product stream.

After the reaction, the resulting products 508 can optionally transferred to a water soluble separation unit 510 wherein the reaction products (wherein the unreacted alcohol and $CO_2$ have been removed) 508 are mixed, or contacted with water 511 and wherein any water soluble products 512, e.g. glycerol, and/or bicarbonate, generated during the reaction are separated from the reaction products that are water insoluble 513. This step can be carried out by any of several suitable methods known in the art, e.g. a water wash and therefore lends itself to conventional methods.

In alternative embodiments, the reaction products are transferred to a static mixer wherein it is mixed with water. The water and reaction product mixture is then transferred to a decanter wherein an oil (lipid) stream comprising the free fatty acids and any unreacted feedstock, and an aqueous stream, comprising bicarbonate, glycerol and/or glycerol derivatives, and any other water soluble reaction products, are formed and are separated.

The aqueous stream (comprising bicarbonate, glycerol and any derivatives thereof) is then transferred to a separating unit wherein glycerol is isolated and removed from the remaining products in the aqueous phase.

In alternative embodiments, following the first stage of the two-stage process, the water insoluble products 513 are transferred to a lipid separation unit 514 wherein the free fatty acids and glycerides and any other lipid products 515, as well any fatty acid alkyl esters, are separated from the remaining water insoluble products 516 by any methods known in the art. The separation technique may be, for example, distillation.

Optionally, any unreacted soapstock isolated in the lipid separation unit 514 can be recycled 517 and mixed unreacted soapstock 501 for subsequent reactions. In alternative embodiments, unreacted feedstock is recycled and the process is repeated until substantially all of the soaps in the soapstock have been converted to free fatty acids and bicarbonate.

Once separated, the free fatty acids and glycerides 515 and any other lipids obtained in the first stage of the process are mixed with water 516 and alcohol 517 in a mixer 518 to form a second reaction mixture 519. In alternative embodiments, the mixture 519 is then fed into the reactor (e.g., the super-critical alcohol reactor) 520 wherein the reaction conditions are such that the one or more of the components of the mixture becomes supercritical, or near-critical. In certain embodiments, for example, the pressure of the reactor is maintained such that the alcohol in the second mixture is prevented from boiling and heated to above the critical temperature of the alcohol, thereby causing the alcohol to become supercritical or near supercritical. In alternative embodiments, the pressure in the reactor is maintained such that the water, alcohol, or both become supercritical or near-critical.

In alternative embodiments, the reactor is operated at a temperature above the super critical temperature of the selected alcohol. For example, when methanol is used as an alcohol, the temperature of the reactor is maintained at a temperature of at least 240° C., since the critical temperature of methanol is 240° C., or when ethanol is used as an alcohol, the temperature of the reactor is maintained at a temperature of at least 243° C., since the critical temperature of ethanol is 213° C., or when propanol is used as an alcohol, the temperature of the reactor is maintained at a temperature of at least 264° C., since the critical temperature of propanol is 264° C., or when isopropanol is used as an alcohol, the temperature of the reactor is maintained at a temperature of at least 236° C., since the critical temperature of isopropanol is 236° C., or when butanol is used as an alcohol, the temperature of the reactor is maintained at a temperature of at least 287° C., since the critical temperature of butanol is 287° C., or when isobutanol is used as an alcohol, the temperature of the reactor is maintained at a temperature of at least 275° C., since the critical temperature of isobutanol is 275° C., or when tert.-butanol is used as an alcohol, the temperature of the reactor is maintained at a temperature of at least 233° C., since the critical temperature of tert.-butanol is 233° C.

In alternative embodiments, the second stage of the two-stage process is carried out at a temperature in the range of between about 150 degrees Celsius to about 300 degrees Celsius and a pressure that is sufficient to keep the alcohol from boiling, for example, a pressure slightly in excess of the vapor pressure of the alcohol of choice at the selected operating temperature (e.g. 20 psig over the vapor pressure). In alternative embodiments, the pressure of the second stage of the two-stage process is in the range of between about 1500 psi to about 2500 psi. In alternative embodiments, the pH of the reaction is in the range of between about 0 to about 7, or anywhere between about pH 0.1 and pH 7.4, or between about pH 0.5 and pH 7.0, or between about 0 and pH 7, or about pH 1, 1.5, 2, 2.5, 3, 3.5, 4, 4.5, 5, 5.5, 6, 6.5, 7, 7.5 or more (or more basic).

In alternative embodiments, the second reaction of the two-stage process can be in the range of between about 1 minute and 4 hours, e.g. between about 10 minutes and 3 hours, between about 20 minutes and 2 hours, or between about 30 minutes and 1 hour. In alternative embodiments, the second reaction is long enough to allow for substantially all of the free fatty acids in the lipid product to undergo esterification, and for substantially all of the esters in the lipid product to undergo transesterification, and not overly long such that the process becomes uneconomical and avoids the generation of undesirable reaction products or degrades the reaction products.

In alternative embodiments, in the second stage of the two-stage process, the free fatty acids are subjected to esterification to form fatty acid alkyl esters. If methanol is used, for example, the fatty acids will be esterified and alkylated to form fatty acid methyl esters, or FAMEs, also called biodiesel.

Any glycerides present in the second reaction mixture are subjected to hydrolysis, alcoholysis, transesterification, or simultaneous hydrolysis/alcoholysis/transesterification, thereby cleaving the fatty acids from the glyceride molecules and esterifying them to from fatty acid alkyl esters. The second reaction slurry would therefore comprise primarily fatty acid alkyl esters, with a proportion of non-esterified fatty acids, along with glycerol generated from the cleaving of any glycerides. The various products from the second reaction can then be separated using any methods known in the art, for example distillation.

The alcohol used in this process can be, for example, methanol, ethanol, propanol, butanol, isopropyl alcohol, sec-butanol, t-butanol, benzyl alcohol, or a combination thereof. In alternative embodiments, alcohols containing 1 to 5 carbons may be preferred, however, there may be specific situations and conditions wherein higher alcohols could be used.

The reactor system can be batch or continuous. In alternative embodiments, any conventional pressure vessel systems can be used, including those that operate in batch and continuous modes; and the process can lend itself to the "conventional" methods for this stage. In addition, a continuous pipe-type or plug-flow reactor can be used to carry out the reaction. In alternative embodiments, the reactor is a pipe with sufficient residence time to allow for the reaction to complete and is operated under the target pressure and temperature range. The pipe allows for reasonable reaction to occur with minimized vessel complexity.

In alternative embodiments, un-reacted alcohol can be separated from the reaction slurry (the second reaction mixture) 519 at this stage and, optionally, recycled for subsequent reactions 522. The alcohol separation may be achieved by any of several known methods in the art, for example a flash separation. In alternative embodiments, the product mixture undergoes a flash process wherein the product mixture is transferred to a flash drum or appropriate or equivalent vessel wherein the pressure is reduced to from the pressure within the reactor, to, for example, about atmospheric pressure, or about less than 14 psi, e.g. less than 1 psi, or about 0.1 psi. The decrease in pressure results in an environment in which the vapor pressure of the alcohol, e.g., methanol, exceeds its external pressure (the pressure of the flash drum or vessel), allowing for the alcohol, e.g., methanol, and water (collectively referred to as "the solvent" in this and subsequent steps) to vaporize or "flash" out of the product mixture.

In certain embodiments, the product slurry 521 (wherein the alcohol has been removed 522) can be fed to a water-solubles separation 523 unit, wherein the product mixture 521 is contacted with water and the water-soluble products 525 are removed from the mixture 521. The method used in the water-solubles separation step can be any of several methods known in the art, e.g. a water wash. Those skilled in the art would recognize that other separation methods would be suitable for this step. Water-soluble products can include, for example, glycerol and glycerol derivatives.

In alternative embodiments, the product mixture (wherein the alcohol and $CO_2$ have been removed) is transferred to a static mixer wherein it is mixed with water. The water and reaction slurry mixture is then transferred to a decanter wherein an oil (lipid) stream, comprising any the fatty acid alkyl esters, e.g. fatty acid methyl esters (FAME), as well as any other lipid products and any unreacted feedstock, and an aqueous stream are formed and are separated.

In alternative embodiments, the aqueous stream (comprising glycerol and any derivatives thereof, any of the alcohol, e.g., methanol that was not removed in the previous alcohol separation step, and water) is then transferred to a glycerol stripping column, e.g. a 4-stage stripping column, in which the aqueous stream is introduced to the top of the column and, upon contacting the bottom of the column is heated such that a vapor phase, comprising primarily the alcohol e.g. methanol and water, is generated and rises to the top of the column where it is removed. In this exemplary embodiment, the column "bottoms" are a primarily a glycerol product that can be, for example, in the range about 80 to 88 wt % glycerol, e.g. about 85% glycerol.

In alternative embodiments, after the water-soluble products are separated, the remaining water-insoluble products 526 (e.g., a lipid stream resulting from the water-washing step) are transferred to a fatty acid alkyl ester (e.g. FAME) separation unit 528 wherein the fatty acid alkyl esters and other products are separated into discreet fractions, e.g., fatty acid alkyl esters 529 and glycerides.

The fatty acids produce in any embodiment of the present invention can be used and/or processed for use in a variety of industrial applications. For example, the fatty acids can be purified and/or separated into individual fatty acids using any suitable technique or method known in the art, e.g. pressing, solvent crystallization, fractional distillation, or the like. The fatty acids can also be converted to various products through additional reaction steps. These include, without limitation, hydrogenation, oxidative cleavage, polymerization, and the like. Exemplary uses of fatty acids and their derivatives include:

Cosmetics and toiletries: can be used directly or, for example, saponified for use in a range of cosmetic and toiletry ingredients such as shampoos, shaving creams etc.

Foods: fatty acids produced in alternative embodiments of the present invention can be used directly or upgraded and/or converted for use as emulsifiers, stabilizers, surface active agents, lubricants, and plasticizers in food products.

Diacids (Dicarboxylic acids): The fatty acids produced in any of the embodiments of the present invention can be converted to diacids (dicarboxylic acids) using any suitable method known in the art. The diacids produced can be used in a range of industrial applications, e.g. as adhesives, plasticizers, gelatinizing agents, hydraulic fluids, lubricants, emollients, and for the production of polymers e.g. nylon and polyurethane foam.

Azelaic acid: A specific diacid, azelaic acid, can be produced, for example, by reacting an oleic acid produced in any embodiment of the present invention with chromic acid, resulting in the oxidative cleavage of the oleic acid to produce azelaic acid, or by the ozonolysis of oleic acid, or any other suitable method known in the art Other industrial applications including ingredients in the production of soaps and synthetic detergents, wetting agents in textile manufacturing, industrial lubricating greases and oils, paints and protective coatings, and as vulcanizing and compounding agents in the production of natural rubber.

Monoglycerides: The free fatty acids produced in any of the embodiments can be used for the production of monoglycerides e.g. by reacting them with glycerol through any suitable method known in the art. This could be achieved either by reacting the "mixed" free fatty acids obtained directly with glycerol or by isolating and/or purifying individual fatty acids (i.e. "cuts" of fatty acids with the same chemical structure) and reacting them with glycerol to produce a uniform mix of monoglycerides. Monoglycerides are useful for a range of industrial and commercial applications e.g. as food and beverage additives and emulsifiers, and as ingredients in personal care and toiletry products.

The fatty acid alkyl esters produced in any of the embodiments of the invention can be used in a variety of commercial and industrial applications. For example, the fatty acid alkyl esters, e.g. fatty acid methyl esters, can be used directly as a fuel (e.g. as a biodiesel fuel) or a fuel additive. The fatty acid alkyl esters may also be subjected to one or more purification and/or separation procedures to generate individual "cuts" or streams of uniform fatty acid alkyl esters (i.e. alkyl esters of the same chemical structure). Theses "chemical" grade alkyl esters can be used in a variety of applications.

The invention will be further described with reference to the following examples; however, it is to be understood that the invention is not limited to such examples.

EXAMPLES

Example 1: Theoretical Yield of Fatty Acids and Fatty Acid Derivatives

This example describes exemplary processes of the invention, and their yields.

A soapstock produced during the chemical refining of a natural oil (or possibly multiple types of natural oils) was obtained from ConAgra Foods, Inc. In order to determine the total fatty acid content of the soapstock and therefore the maximum theoretical yield of fatty acids and/or fatty acid derivatives, multiple samples of the soapstock were reacted with methanol in the presence of a sulfuric acid catalyst. The reaction conditions of each of the reactions are shown in Table 1. The object of the reaction was to acidify the soaps present in the soapstock to generate free fatty acids and carbonate. The resulting free fatty acids would then be esterified in with the methanol to produce fatty acid methyl esters (FAME). The reaction conditions were also suitable for the conversion of any glycerides phospholipids, or other lipid products in the soapstock to FAME via acidification, esterification, transesterification, or a combination thereof

TABLE 1

| Soapstock (by wt. %) | 20 |
| MeOH (by wt. %) | 80 |
| Catalyst (% wt of soapstock) | 20 |
| Reactor Temperature (° C.) | 105 |
| Reaction Time (hrs) | 4 |

The FAME in the resulting product mixture was then extracted using a hexane extraction wherein the produce mixture was contacted with hexane three separate times, each time separating the hexane phase from the non-hexane phase. The hexane solubles comprising the FAME were analyzed using gas chromatography (GC) to determine the weight of the FAME relative to the weight of the soapstock in the reaction mixture. The results of the GC analysis are shown in table 2.

TABLE 2

| Run | % FAME in Hexane Phase | FAME Yield As a % of the Weight of the Soapstock Sample |
| --- | --- | --- |
| 1 | 75.1 | 54.4 |
| 2 | 73.1 | 51.7 |
| 3 | 67.4 | 48.0 |
| Average | 71.9 | 51.4 |

The FAME yield represents the maximum theoretical yield for subsequent examples in which the presently disclosed invention is used to produce free fatty acids and derivatives thereof from soapstocks.

Example 2: Single Stage Conversion of Soapstock to FFA with Water and $CO_2$

This example describes exemplary processes of the invention.

Multiple runs were conducted under various reaction conditions using the same soapstock from Example 1, obtained from ConAgra Foods, Inc. The soapstock samples were mixed with water prior to being reacted in the presence of $CO_2$. The $CO_2$ was supplied to the reaction using either gaseous $CO_2$ or dry ice. The % yield of fatty acids (FFA) was calculated based on the theoretical yields obtained by reacting samples of the soapstock with methanol and sulfuric acid (see Example 1). Table 3 shows the reaction conditions and the resulting FFA yields.

TABLE 3

| Run | Quantity of soapstock reacted (g) | Temperature (° C.) | Pressure (psi) | Reaction time (min) | % conversion | $CO_2$ source |
| --- | --- | --- | --- | --- | --- | --- |
| 1 | 16.1 | 22 | 875 | 90 | 55.4 | Dry Ice |
| 2 | 12.6 | 40 | 1125 | 137 | 47 | |
| 3 | 17.2 | 22 | 700 | 60 | 29.3 | |
| 4 | 15.3 | 40 | 800 | 60 | 41.4 | Gaseous |
| 5 | 18.0 | 26 | 820 | 32 | N/A | $CO_2$ |
| 6 | 16.2 | 21 | 800 | 75 | 52 | |

Example 3: Single Stage Conversion of Soapstock Surrogate (Sodium Oleate) to FFA with Water and $CO_2$ This example describes exemplary single stage processes of the invention.

Multiple runs were conducted under various reaction conditions using 100% sodium oleate as a surrogate for soapstock. The sodium oleate samples were mixed with water prior to being reacted in the presence of $CO_2$. The $CO_2$ was supplied to the reaction using either gaseous $CO_2$ or dry ice. The % yield of fatty acids (FFA) was determined based by comparing the mass of FFA produced in the reaction to the molar mass of the fatty acids contained in the surrogate. Table 4 shows the reaction conditions and the resulting FFA yields.

TABLE 4

| Run | Quantity of sodium oleate reacted (g) | Temperature (° C.) | Pressure (psi) | Reaction time (min) | % conversion | $CO_2$ source |
| --- | --- | --- | --- | --- | --- | --- |
| 1 | 10.3 | 40 | 1200 | 60 | 99 | Dry Ice |
| 2 | 13.5 | 40 | 1200 | 60 | 78.4 | |
| 3 | 11.2 | 40 | 1270 | 60 | 88.5 | |
| 4 | 11.8 | 20 | 840 | 60 | 74 | |
| 5 | 11.9 | 20 | 830 | 180 | 97.3 | |
| 6 | 11.8 | 22 | 850 | 60 | 87.7 | |
| 7 | 5 | 22 | 840 | 60 | 111 | |
| 8 | 10 | 80 | 2000 | 60 | 72 | |
| 9 | 10.1 | 22 | 630 | 60 | 97 | Gaseous |
| 10 | 10 | 40 | 720 | 60 | 92.5 | $CO_2$ |
| 11 | 9.9 | 20 | 730 | 10 | 89.1 | |
| 12 | 10 | 21 | 760 | 5 | 93.5 | |
| 13 | 10.3 | 21 | 100 | 10 | 93.8 | |
| 14 | 9.8 | 23 | 300 | 10 | 90.1 | |

Example 4: Single Stage Conversion of Soapstock Surrogate (Potassium Octanoate) to FFA with Water and $CO_2$ This example describes exemplary single stage processes of the invention.

Multiple runs were conducted under various reaction conditions using 100% potassium octanoate as a surrogate for soapstock. The potassium octanoate samples were mixed with water prior to being reacted in the presence of $CO_2$. The $CO_2$ was supplied to the reaction using dry ice. The % yield of fatty acids (FFA) was determined based by comparing the mass of FFA produced in the reaction to the molar mass of the fatty acids contained in the surrogate. Table 5 shows the reaction conditions and the resulting FFA yields.

TABLE 5

| Run | Quantity of potassium octanoate reacted (g) | Temperature (° C.) | Pressure (psi) | Reaction time (min) | % conversion | $CO_2$ source |
|---|---|---|---|---|---|---|
| 1 | 15.2 | 20 | 720 | 1440 | 90 | Dry Ice |
| 2 | 16.9 | 40 | 1060 | 60 | 48.5 | |
| 3 | 14.7 | 45 | 1070 | 60 | 64.8 | |
| 4 | 13.7 | 41 | 1250 | 60 | 78.8 | |

Example 5: Single Stage Conversion of Soapstock Surrogate (Potassium Stearate) to FFA with Water and $CO_2$ This example describes exemplary single stage processes of the invention.

Multiple runs were conducted under various reaction conditions using 100% potassium stearate as a surrogate for soapstock. The potassium stearate samples were mixed with water prior to being reacted in the presence of $CO_2$. The $CO_2$ was supplied to the reaction using dry ice. The % yield of fatty acids (FFA) was determined based by comparing the mass of FFA produced in the reaction to the molar mass of the fatty acids contained in the surrogate. Table 6 shows the reaction conditions and the resulting FFA yields.

TABLE 6

| Run | Quantity of potassium stearate reacted (g) | Temperature (° C.) | Pressure (psi) | Reaction time (min) | % conversion | $CO_2$ source |
|---|---|---|---|---|---|---|
| 1 | 19.1 | 10 | 660 | 1080 | N/A | Dry Ice |
| 2 | 10.1 | 40 | 1260 | 60 | 43.7 | |
| 3 | 11.9 | 20 | 800 | 70 | 17.1 | |

Example 6: Single Stage Conversion of Soapstock Surrogate (Sodium Stearate) to FFA with Water, $CO_2$ and a Phase Transfer Catalyst This example describes exemplary single stage processes of the invention.

Multiple runs were conducted under various reaction conditions using 100% potassium stearate as a surrogate for soapstock. The potassium stearate samples were mixed with water prior to being reacted in the presence of $CO_2$. The $CO_2$ was supplied to the reaction using dry ice. Ammonium chloride and tetraethylammonium bromide were used as phase transfer catalysts (PTC). The sodium stearate was also mixed with 50% by mass ethanol as a solvent prior to reacting. The % yield of fatty acids (FFA) was determined based on the mass of FFA produced in the reaction to the molar mass of the fatty acids contained in the surrogate. Table 7 shows the reaction conditions and the resulting FFA yields.

TABLE 7

| Run | Quantity of potassium stearate reacted (g) | Temperature (° C.) | Pressure (psi) | Reaction time (min) | % conversion | $CO_2$ source |
|---|---|---|---|---|---|---|
| PTC: Ammonium chloride (5% wt/wt) | | | | | | |
| 1 | 13.6 | 21 | 800 | 60 | 6.3 | Dry Ice |
| 2 | 11.7 | 40 | 1170 | 60 | 30.4 | |
| PTC: Tetraethylammonium bromide (5% wt/wt) | | | | | | |
| 3 | 14.4 | 36 | 1100 | 60 | 12.7 | Dry Ice |
| 4 | 10.4 | 40 | 1000 | 60 | 8.2 | |

Example 7: 2-Stage Conversion of Soapstock

This example describes exemplary two-stage processes of the invention.

Soapstock obtained from ConAgra Foods, Inc. (the same soapstock from Example 1) was reacted in a 2-stage process. In the first stage reaction (Stage 1), multiple runs of the soapstock were reacted with water and $CO_2$. The resulting product mixture was then extracted 3-times using chloroform to remove any lipid material from the product mixture (including free fatty acids and esters, e.g. glycerides and/or phospholipids). The chloroform phase (comprising the lipids) was then dried, allowing the chloroform to evaporate and leaving the lipid material. The lipid material was then weight prior to being reacted with supercritical methanol (Stage 2). Table 8 shows the reaction conditions of the Stage 1 reactions.

TABLE 8

| Soapstock (by wt. %) | 20 |
|---|---|
| Water (by wt. %) | 80 |
| $CO_2$ (% wt of soapstock) | 20 |
| Reactor Temperature (° C.) | 105 |

| Reaction Time (hrs) | Run |
|---|---|
| 1 | 2.25 |
| 2 | 2.5 |
| 3 | 4 |

For each run, the lipid material obtained from the Stage 1 reaction was then reacted with supercritical methanol to esterify the free fatty acids and transesterify the esters (e.g. glycerides and phospholipids. The reaction conditions for all of the Stage 2 reactions (the conditions were the same for each run) are defined in Table 9.

TABLE 9

| Lipid Material, i.e. Chloroform Solubles from Stage 1 (by wt. %) | 20 |
|---|---|
| MeOH (by wt. %) | 80 |
| Reactor Pressure (psi) | 2000 |
| Reactor Temperature (° C.) | 280 |
| Reaction Time (hrs) | 1 |

During the Stage 2 reactions, FFAs in the lipid material from Stage 1 were esterified with methanol to form fatty acid methyl esters (FAME). The esters in the lipid material from the Stage 1 reactions were transesterified to form FAME. In order to determine the % conversion of FFAs and esters in the lipid material from the Stage 1 reactions to FAME, the resulting product mixtures from the Stage 2 reactions were subjected to a hexane extraction process. Each Stage 2 product mixture was contacted with hexane to remove the FAME from the other components of the product mixtures. This process was repeated 3-times for each Stage 2 product mixture. The hexane solubles (comprising FAME) were then analyzed using gas chromatography (GC) to determine the % yield of FAME from the soap stock, based on the maximum theoretical yield as determined in Example 1. Table 9 shows results of the hexane extraction for each of the Stage 2 runs and the % conversion of soaps and lipid materials in the soapstock to FAME. The Run numbers correspond to the Run numbers in Table 8.

TABLE 10

| Run | % FAME in hexane | % FAME conversion |
|-----|------------------|-------------------|
| 1 | 60.8 | 51.3-57.9 |
| 2 | 67.1 | 81.5-92.6 |
| 3 | 61.9 | 73.4-83.4 |

A number of embodiments of the invention have been described. Nevertheless, it will be understood that various modifications may be made without departing from the spirit and scope of the invention. Accordingly, other embodiments are within the scope of the following claims.

What is claimed is:

1. A method or industrial process for the production of free fatty acids, fatty acid alkyl esters, or a combination thereof from a soap or a soapstock comprising soaps or salts of fatty acids, the method or industrial process consisting essentially of:
   (a) providing a reaction mixture comprising a soap or a soapstock, water, carbon dioxide ($CO_2$),
   and providing a phase transfer catalyst, wherein the water and the $CO_2$ react to form carbonic acid; and
   (b) reacting the reaction mixture and the phase transfer catalyst at:
   a temperature in a range of between about 0° C. and about 50° C., and
   a pressure in a range of between about 0 psi and about 3000 psi,
   for a time that is sufficient to provide for acidification of a soap or a soapstock in the reaction mixture,
   thereby generating a free fatty acid and a bicarbonate from the soap or soapstock in the reaction mixture.

2. The method or industrial process of claim 1, wherein the soapstock further comprises glycerides and/or phosphatides.

3. The method or industrial process of claim 1, wherein in step (b) the reaction mixture is reacted at a temperature in a range of between about 5° C. to about 40° C.

4. The method or industrial process of claim 1, wherein in step (b) the reaction mixture is reacted at a pressure in the range of between about 50 psi and about 2500 psi.

5. The method or industrial process of claim 1, wherein in step (b) the time that is sufficient to provide for acidification of a portion of the soaps is between about 0 to about 24 hours.

6. The method or industrial process of claim 5, wherein in step (b) the time that is sufficient to provide for acidification of a portion of, or substantially all of, the soaps is between about 0 to about 12 hours.

7. The method or industrial process of claim 1, wherein the soapstock is derived from a crude vegetable oil.

8. The method or industrial process of claim 1, wherein an amount of water in the reaction mixture is between about 1 mol to about 200 mol per mol of soapstock.

9. The method or industrial process of claim 1, wherein an amount of $CO_2$ in the reaction mixture is between about 1 mol to about 70 mol per mol of soapstock.

10. The method or industrial process of claim 1, wherein an amount of $CO_2$ in the reaction mixture is about 10 mol per mol of soapstock.

11. The method or industrial process of claim 1, wherein the phase transfer catalyst in the reaction mixture is between about 1 wt % to about 50 wt % of the reaction mixture.

12. The method of claim 1, wherein the phase transfer catalyst in the reaction mixture is about 1 wt % of the reaction mixture.

13. The method or industrial process of claim 1, wherein the phase transfer catalyst comprises an ammonium chloride.

14. The method or industrial process of claim 1, wherein the phase transfer catalyst is selected from the group consisting of ammonium chloride, tetrabutyl-ammonium bromide, and tetraethyl-ammonium bromide.

15. The method or industrial process of claim 3, wherein in step (b) the reaction mixture is reacted at a temperature in the range of between about 10° C. to about 30° C., or about 15° C. to about 25° C.

16. The method or industrial process of claim 4, wherein in step (b) the reaction mixture is reacted at a pressure in the range of in the range of between about 100 psi to about 2000 psi, about 150 psi to about 1500 psi, about 200 psi to about 1000 psi, about 250 psi to about 800 psi, or about 300 psi to about 600 psi.

17. The method or industrial process of claim 5, wherein in step (b) the time that is sufficient to provide for the acidification of substantially all of the soaps is between about 0 to about 24 hours.

18. The method or industrial process of claim 6, wherein in step (b) the time that is sufficient to provide for the acidification of a portion of, or substantially all of, the soaps is between about 1 hour and about 8 hours, between about 3 hours and 5 hours, between about 5 minutes and one hour, between about 2 minutes to about 20 minutes, or between about 0 minutes to about 1 minute.

19. The method or industrial process of claim 8, wherein the amount of water in the reaction mixture is between about 10 and 100 mol per mol, of soapstock.

20. The method or industrial process of claim 9, wherein the amount of $CO_2$ in the reaction mixture is between about 10 mol to about 60 mol per mol.

21. The method or industrial process of claim 10, wherein the amount of $CO_2$ in the reaction mixture is about 20, 30, 40, 50, 60, 70, 80, 90 or 100 or more mol per mol, of soapstock.

22. The method or industrial process of claim 12, wherein the phase transfer catalyst in the reaction mixture is about 5, 10, 20, 30, 40, 50, 60, 70, 80 or 90 wt % of the reaction mixture.

23. The method or industrial process of claim 7, wherein the crude vegetable oil selected from the group consisting of: soybean oil, palm oil, canola oil, rapeseed oil, wheat germ oil, safflower oil, peanut oil, cottonseed oil, sunflower oil, and algae oil.

24. The method or industrial process of claim 1, further comprising esterifying the free fatty acid.

25. The method or industrial process of claim 2, wherein the soapstock further comprises glycerides and/or phosphatides and the glycerides and/or phosphatides are subjected to hydrolysis and/or esterification, thereby generating free fatty acids and/or fatty acid alkyl esters.

* * * * *